(12) United States Patent
Farkas et al.

(10) Patent No.: US 7,316,904 B1
(45) Date of Patent: Jan. 8, 2008

(54) AUTOMATED PAP SCREENING USING OPTICAL DETECTION OF HPV WITH OR WITHOUT MULTISPECTRAL IMAGING

(75) Inventors: Daniel L. Farkas, Los Angeles, CA (US); Elliot S. Wachman, Lakewood, NJ (US); Jill Wachman, Lakewood, NJ (US); Miriam Farkas, Los Angeles, CA (US); Stanley J. Geyer, Pittsburgh, PA (US)

(73) Assignee: Chromodynamics, Inc., Lakewood, NJ (US)

( * ) Notice: Subject to any disclaimer, the term of this patent is extended or adjusted under 35 U.S.C. 154(b) by 393 days.

(21) Appl. No.: 10/881,224

(22) Filed: Jun. 30, 2004

(51) Int. Cl.
*C12Q 1/68* (2006.01)

(52) U.S. Cl. .......................... 435/6; 435/40.5

(58) Field of Classification Search ............. 435/6, 435/7.1, 40.5
See application file for complete search history.

(56) References Cited

U.S. PATENT DOCUMENTS

| | | | |
|---|---|---|---|
| 4,017,192 A | 4/1977 | Rosenthal | |
| 4,523,278 A | 6/1985 | Reinhardt et al. | |
| 4,998,284 A | 3/1991 | Bacus et al. | |
| 5,257,182 A | 10/1993 | Luck et al. | |
| 5,287,272 A | 2/1994 | Rutenberg et al. | |
| 5,544,650 A | 8/1996 | Rutenberg et al. | |
| 5,715,327 A | 2/1998 | Wilhelm et al. | |
| 5,740,270 A | 4/1998 | Rutenberg et al. | |
| 5,784,162 A | 7/1998 | Cabib et al. | |
| 5,796,512 A | 8/1998 | Wachman et al. | |
| 5,797,130 A | 8/1998 | Nelson et al. | |
| 5,841,577 A | 11/1998 | Wachman et al. | |
| 5,933,519 A | 8/1999 | Lee et al. | |
| 5,939,278 A | 8/1999 | Boon et al. | |
| 6,027,905 A | 2/2000 | Keesee et al. | |
| 6,143,512 A | 11/2000 | Markovic et al. | |
| 6,181,414 B1 | 1/2001 | Raz et al. | |
| 6,294,331 B1 | 9/2001 | Ried et al. | |
| 6,327,377 B1 | 12/2001 | Rutenberg et al. | |
| 6,355,424 B1 | 3/2002 | Lorincz et al. | |
| 6,373,568 B1 | 4/2002 | Miller et al. | |
| 2001/0020132 A1 | 9/2001 | Nordsrom et al. | |
| 2001/0053958 A1 | 12/2001 | Ried et al. | |
| 2002/0001080 A1 | 1/2002 | Miller et al. | |
| 2002/0019723 A1 | 2/2002 | Zwiegincew et al. | |
| 2002/0081013 A1 | 6/2002 | Raz | |
| 2002/0097388 A1 | 7/2002 | Raz | |
| 2002/0106685 A1 | 8/2002 | Henning et al. | |
| 2002/0123845 A1 | 9/2002 | Henning et al. | |

OTHER PUBLICATIONS

Lerner et al. Proceedings of the WTEC, Tissue Engineering Workshop, NIH, Jun. 2000, pp. 206-220.*
Shonat et al., Near-Simultaneous Hemoglobin Saturation and Oxygen Tension Maps in Mouse Brain Using an AOTF Microscope, Biophysical Journal, Sep. 1997, 1223-1231, vol. 73.
Wachman, et al., AOTF Microscope for Imaging with Increased Speed and Spectral Versatility, Biophysical Journal, Sep. 1997, 1215-1222, vol. 73.
Shonat, et al., Near-Simultaneous Hemoglobin Saturation and Oxygen Tension Maps in the Mouse Cortex During Amphetamine Stimulation, Plenum Press, 1998, 149-158.

* cited by examiner

*Primary Examiner*—Ali R. Salimi
(74) *Attorney, Agent, or Firm*—Thorp Reed & Armstrong, LLP

(57) ABSTRACT

The present disclosure involves a method of preparing a cervical sample for medical examination in which a papanicolaou stained sample is additionally stained with a label targeted to one or more high risk cancer markers to allow for optical detection of the human papilloma virus. That optical detection can be combined with morphometric detection of abnormal cells, which may be improved by multispectral imaging using an acousto-optic tunable filter. Several variations of screening methods and an apparatus for performing the methods are disclosed.

7 Claims, 4 Drawing Sheets

AUTOMATED PAP SCREENING USING OPTICAL DETECTION OF HPV WITH OR WITHOUT MULTISPECTRAL IMAGING

BACKGROUND

The present disclosure is broadly concerned with automated papanicolaou (Pap) screening technology.

Cervical cancer is the leading cause of death of women in third world countries. In the U.S., approximately 13,000 women were diagnosed with cervical cancer in the year 2002 alone. The Pap test is used to screen for cervical cancer, and is generally considered to be the most effective screening technique ever developed for any cancer. Current medical practice calls for each female above adolescence to receive one Pap test annually. This amounts to approximately 50 million tests a year in the U.S., and approximately 60 million abroad.

Of the tests done each year in the U.S., approximately 7% display abnormalities that require additional clinical follow-up. A substantially greater percentage reveal other abnormalities that do not necessarily represent precancerous changes, such as low grade squamous intraepithelial lesions (LSIL) and atypical squamous cells of undetermined significance (ASCUS), but may nonetheless assume importance in risk stratification.

Of the nearly one hundred strains of Human Papilloma Virus (HPV) that have been identified to date, a small subset has been recognized as high-risk, with a strong correlation to development of precancerous changes of the cervix known as high grade squamous inter-epithelial lesions (HSIL). Indeed, infection with a high-risk HPV constitutes the major risk factor for development of cervical cancer.

The conventional approach to Pap screening is not able to detect infection with high-grade HPV, nor is it able to distinguish reliably between ASCUS and HSIL. In response to this deficiency of conventional microscopy, the National Cancer Institute sponsored a multicenter ASCUS/LSIL Triage Study (ALTS) to determine optimum strategies for early detection of women at risk of developing cervical cancer. The triage study tested three follow up procedures: immediate colposcopy, HPV testing, and conservative management with repeating of the Pap smear examination. The trial results concluded that HPV testing is a preferred option in the management of women with ASCUS because of its sensitivity and specificity as a disease marker.

In the ALTS study, HPV was detected utilizing a hybrid capture method (Digene Corporation) in which residual fluid from liquid-based Pap smear specimens is placed into a microwell plate, and the presence of selected HPV strains produces chemiluminescence. Microscopic visualization of the infected cells in the specimen is not possible. Immunohistochemical staining is an alternative approach that has been used for HPV detection. This approach allows the pathologist to visualize the infected cells, however sensitivity and specificity is reduced in comparison to the hybrid capture method. In addition, the colorimetric appearance of the sample is quite different from the customary Pap smear.

Because in the United States approximately 50 million women undergo Pap testing to screen for the presence of cancer or high-risk precursor lesions, examination of this enormous number of slides requires a suitably large number of well-trained cytotechnologists. Unfortunately, the availability of competent cytotechnologists is decreasing. Additionally, each slide to be examined by the cytotechnologist contains 200,000 to 500,000 cells, which must ideally all be checked. The repetitive nature of this job makes it difficult to prevent decay in attentiveness and performance towards the end of the workday. As a result, there has been an effort to develop automated Pap screening technology to augment the decreasing number of competent cytotechnologists as well as to enhance the consistency of the screening and throughput of all of the slides.

Because a given Pap smear is often viewed quite differently by different pathologists, as clearly reflected in the structure of the Bethesda classification system, the need for a rigorous method of quantifying diagnostic criteria has long been recognized in this profession. Automated Pap screening that relies on computer-based algorithms has the potential for addressing this problem.

Presently, there is one fully automated screening system that has received FDA approval, namely, TriPath Imaging, of Burlington, N.C. Although numerous studies of the TriPath system have appeared in professional literature, the bulk of these studies have concentrated on assessing the sensitivity of this automated instrument. Performance of the TriPath system has been acceptable in this respect. However, the specificity of the TriPath system has not produced nearly as acceptable results. In its FDA approval usage, the TriPath system can "sign-off" on a maximum of 25% of the slides it reviews as requiring no further review. While this may provide modest time savings for a high-volume pathology laboratory, given that 90-95% of the slides screened in a typical laboratory are truly normal, the ability to sign off on only 25% falls far short from what is needed by an automated system.

The TriPath system uses straightforward morphological criteria for assessing cells that are potentially problematic, choosing those cells whose nuclei are deemed to be unusually large and optically dense. These computational algorithms are not capable of accurate, reliable results when confronted with the frequent occurrence of uneven staining and overlapping clumps of cells.

SUMMARY

The present disclosure provides for an automated Pap screening system using optical detection of HPV. The optical detection of HPV may be used with or without traditional morphological analysis to provide greater specificity and sensitivity in screening for high-risk cancer cells. The traditional morphological analysis may be improved by providing high speed multispectral imaging.

One aspect of the present disclosure is a method of preparing a sample for medical examination which comprises staining the sample with a papanicolaou stain and before, after, or simultaneously, staining the sample with at least one label enabling optical detection of human papilloma virus. The at least one label may be an immunofluorescence label. A plurality of labels could be used each targeted to a high risk cancer marker. The plurality of labels may be chosen from a group consisting of dyes that emit in the infrared region of the spectrum, phosphorescent probes, or labels with unique emission properties distinguishable even in the ultra-violet or visible region from papanicolaou emissions.

Another aspect of the present disclosure is a method of screening for human papilloma virus in a medical sample comprising optically detecting emissions from the medical sample for signs of the human papilloma virus. The optically detecting emissions may include optically detecting emissions from labels that emit in the infrared region of the spectrum, phosphorescent probes and labels with unique emission properties distinguishable even in the visible region from papanicolaou emissions. The method of screening may additionally include transmission imaging in the visible range from the medical sample for morphological signs of the high risk cells. The optically detecting of emissions and transmission imaging may be, and is preferably, performed automatically. The transmission imaging in the visible range may include imaging emissions at a plurality of wavelengths using, for example, an AOTF.

Another aspect of the present disclosure of screening for human papilloma virus in a medical sample is comprised of transmission imaging in the visible range from the medical sample for morphological signs of the human papilloma virus and imaging emissions from a label having emission properties distinguishable from the emissions in the visible range from the medical sample for signs of the human papilloma virus. The imaging of emission having distinguishable properties includes imaging emissions from labels that emit in the infrared region of the spectrum, imaging emissions from phosphorescent probes and imaging emissions in the visible range which are distinguishable from the other emissions, e.g. background emissions, in the visible range.

Another aspect of the present disclosure is a method of generating data for use in a papanicolaou screening method from a slide containing a sample of papanicolaou stained-optically detectably labeled cells comprising detecting optically detectable signals from the sample and recording the location of any detected signals. The method of generating data may additionally comprise generating a series of images of the papanicolaou stained cells corresponding to a plurality of wavelengths for each recorded location. Preferably, the detecting and generating are performed automatically.

The present disclosure is also directed to a screening method for use in connection with a slide containing a sample of papanicolaou stained-optically detectably labeled cells comprising detecting any optically detectable signals from the sample corresponding to the possible presence of any high-risk cancer marker (such as the human papilloma virus), recording the location of any detected signals, generating a series of images corresponding to a plurality of wavelengths for each recorded location in transmission illumination of the papanicolaou stained cells, analyzing the series of images for spectral and morphological content and classifying each series of images from each location. Preferably, the detecting, generating, analyzing and classifying are performed automatically.

BRIEF DESCRIPTION OF THE DRAWINGS

To enable the present disclosure to be easily understood and readily practiced, the present disclosure will now be described for purposes of illustration and not limitation, in connection with the following figures wherein.

DETAILED DESCRIPTION

Figure 1:
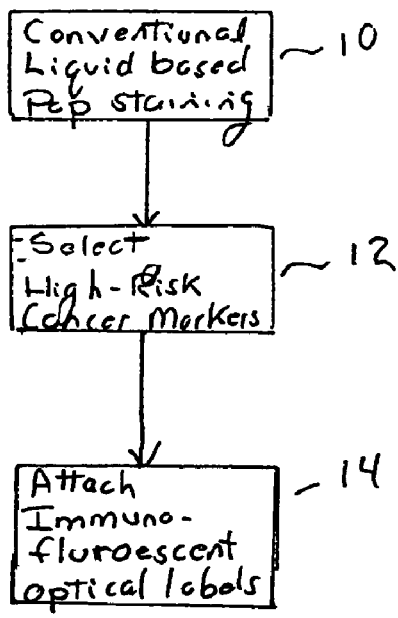
FIG. 1 is a diagram illustrating the preparation of slides according to the present disclosure.

One aspect of the present disclosure is slide preparation. Referring to FIG. 1, a slide is prepared using conventional liquid-Pap preparation techniques at step 10. To the Pap stain, however, an additional labeling mixture is added which contains, for example, at least one, colored, immunofluorescence dye selective to at least one high risk cancer marker. Preferably a plurality of multi-colored, immunofluorescence dyes selective to a cocktail of different high risk cancer marker antibodies is used. The high risk cancer marker of the present disclosure can include a cocktail of markers consisting of all the known oncogenic HPV strains, as well as any other cellular cancer markers known in the art. DNA, protein or other cellular cancer markers may be used. At step 12 a determination is made as to the markers of interest. At step 14, immunofluorescent optical labels are attached. The result is a single slide containing both a conventional Pap stain and the high-risk immunofluorescence labels. Those of ordinary skill in the art will recognize that the slide can be prepared by performing step 14 prior to step 10, or steps 10 and 14 can be performed together. The sequence of steps as shown in FIG. 1 is not of significance.

To enable the colabeling of the Pap stained sample with optical immunofluorescence labeling, the added label or labels should not interfere with the appearance of the slide as viewed in conventional transmission illumination. If the dye absorbs heavily in the visible region of the spectrum, the color of the labeled cells may be altered from what the pathologist is accustomed to seeing. It is also desirable that the label be chosen in a manner in which there be virtually no fluorescence background produced by the Pap stain itself. Otherwise, it may be difficult to distinguish readily those cells containing the marker of interest.

Given that the Pap stain fluoresces broadly throughout the visible region, the label used could be one or a combination of the following:

a) a dye that emits in the infrared region of the spectrum, for example, Cyanine-7;

b) a phosphorescent probe, such as Europium chelate, in conjunction with a flash lamp for excitation and a gated-shutter for detection. This method would allow temporal separation of the labeled marker from the underlying background. Although eosin, one of the main constituents of the Pap stain, is also phosphorescent, because its phosphorescence maximum occurs at about 680 nm, it may be distinguished from the desired label signal by either its spectrum or its phosphorescence lifetime;

c) a label with unique emission properties (such as those based on quantum dot technology) that enables it to be distinguished spectrally even in the visible region where there is also Pap fluorescence present. While examples have been given, those with ordinary skill in the art will recognize that a variety of dyes that emit in the infrared region of the spectrum, phosphorescent probes and labels with unique emission properties may be used for immunofluorescence labeling.

Multiple labels may be used with different cocktails of markers attached to each to derive more diagnostic information about the cells under study. To acquire these multiple color fluorescence labels swiftly, it is desirable that the optical signal produced be sufficiently large. A method of fluorescence signal amplification (such as tyramide signal amplification (TSA)) may therefore also be included as part of the labeling. While TSA has been given as a method of fluorescence signal amplification, those of ordinary skill in the art will recognize that other methods of fluorescence signal amplification may be used.

After the slide is prepared as discussed above, the slide is then placed into a cassette (not shown in FIG. 2) containing numerous such slides from different patients. The cassette is placed onto a slide loader (not shown) of an automated multispectral/fluorescence imaging system (discussed below in conjunction with FIGS. 3 and 4). From the cassette, the slide is preferably automatically loaded onto the imaging system as shown by step 16 in FIG. 2.

The slide, or more precisely the sample on the slide, is imaged at step 18 at many different locations, at both high and low magnification, using two imaging modalities: multispectral transmission imaging and epi-fluorescence imaging in each of the fluorescence channels used for labeling. This process is repeated at numerous locations on the slide. This step 18 may be referred to as a data gathering or data generating step.

An automated microscope is the basis of the imaging system of the present disclosure. XY stage movement, stage focus, objective turret position, light source and filter cube position are all under automated control, with changes made in a minimum amount of time, so that image acquisition is performed automatically under computer control. Automatic slide handling is also beneficial, including mounting, marking and dismounting of slides.

An AOTF imaging module or illumination module is used to provide the spectral imaging capabilities. Examples of the modules which may be used are described in U.S. Pat. No. 5,796,512 and U.S. Pat. No. 5,841,577 which are incorporated herein by reference.

Spectral imaging is a technique in which multiple pictures of a given scene are acquired, each at a successively different wavelength. The resulting "cube" of image information gives a wealth of information that would not otherwise be available from a conventional single color image. This technique has been used to a great advantage in military, industrial, and biomedical applications. In this disclosure, spectral imaging is applied to the examination of Pap smears to provide morphological and color information for cell classification that is not possible with conventional single images.

Spectral imagining technology can loosely be divided into those that are band sequential (where the individual wavelength images are taken one after another) and those that are non-sequential (where multiple image data is acquired, and then subsequently transformed to provide spectral image information). Examples of the former include interference filter wheels, liquid crystal tunable filters (LCTFs) and AOTFs; example of the latter include Fourier transform imaging spectroscopy (FTIS) and tomographic imaging.

While LCTFs have broad tuning capabilities, their bandwidth is fixed, and switching times are typically 50 milliseconds. Interference filter wheels are limited to a predetermined set of wavelength passbands and have similar switching times. In FTIS, a Sagnac interferometer is used to acquire interferometric imaging data at a variety of interferometer settings, and the resulting data Fourier transformed to provide a spectral image set with upwards of 50 bands ranging between 400 and 700 nm. Typical data sets require at least 30 seconds to acquire. In tomographic imaging, light is bounced off a diffraction grating and the various multiple diffraction orders are separated and captured on a single CCD chip for subsequent processing and extraction of the contained spectral information, a computationally intense procedure.

Unlike those techniques, AOTFs have the capability for broad tunability together with variable bandwidth operation, and sub-millisecond switching times. The present disclosure is an AOTF-based imaging system, which docks easily to the camera port of most fluorescence microscopes. Image fidelity is excellent, the device can be tuned from 450 nm to 800 nm, bandwidths can be varied from at each wavelength, and wavelengths can be changed in ~50 microseconds.

A brief illustration will serve to illustrate the importance of the very fast switching time of the AOTF for the present application. Competing band sequential multispectral technologies (liquid crystal tunable filters, interference wheels) require a minimum of 50 milliseconds to switch between wavelengths. A typical daily screening quota for one experienced cytotechnologist is approximately 80 slides, each of which must be imaged at approximately 65 different locations per slide. If 30 different wavelength images are taken at each such location, the daily time savings achieved in using an AOTF relative to a 50 millisecond switching device amounts to nearly 2 hours per cytotechnologist.

Additionally, it should be noted that the AOTF, like other band sequential spectral imaging technologies, also allows variation in system response with wavelength to be compensated for by varying exposure time. It thereby ensures a signal-to-noise ratio that is equal throughout the tuning range. In addition, acquisition can be restricted to a subset of wavelengths of greatest importance, thus minimizing the total acquisition time. The two non-band-sequential techniques mentioned above do not have either of these capabilities.

Figure 2:
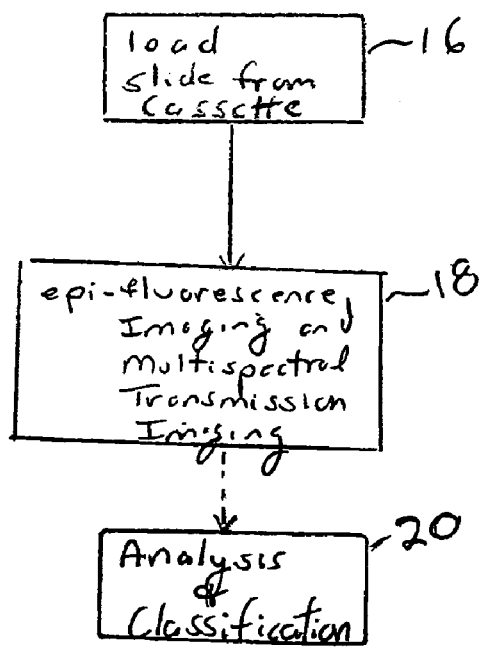
FIG. 2 is a diagram illustrating the steps of the method of the present disclosure.

The images acquired with each modality at each location are analyzed using any known available techniques including for example spectral morphometric and image texture analysis, and an overall classification is determined at step 20 in FIG. 2. The results are recorded, and the slide is removed and sorted by classification before the next slide is loaded onto the instrument.

Image analysis and classification may include any number of steps. Examples of some steps which may be included are: nuclear segmentation, in which the imaged nuclear regions of greatest significance for classification are distinguished from amongst the intercellular and cytoplasmic regions; spectral/morphometric analysis, in which a combination of both spectral and morphometric features are used to grade nuclei by their degree of abnormality; image texture analysis, in which image texture features are used to refine this classification; and results presentation, in which the results for each slide are recorded and stored (with the cell also perhaps physically marked in each suspicious location). These steps are meant to be exemplary and not inclusive.

Figure 3:
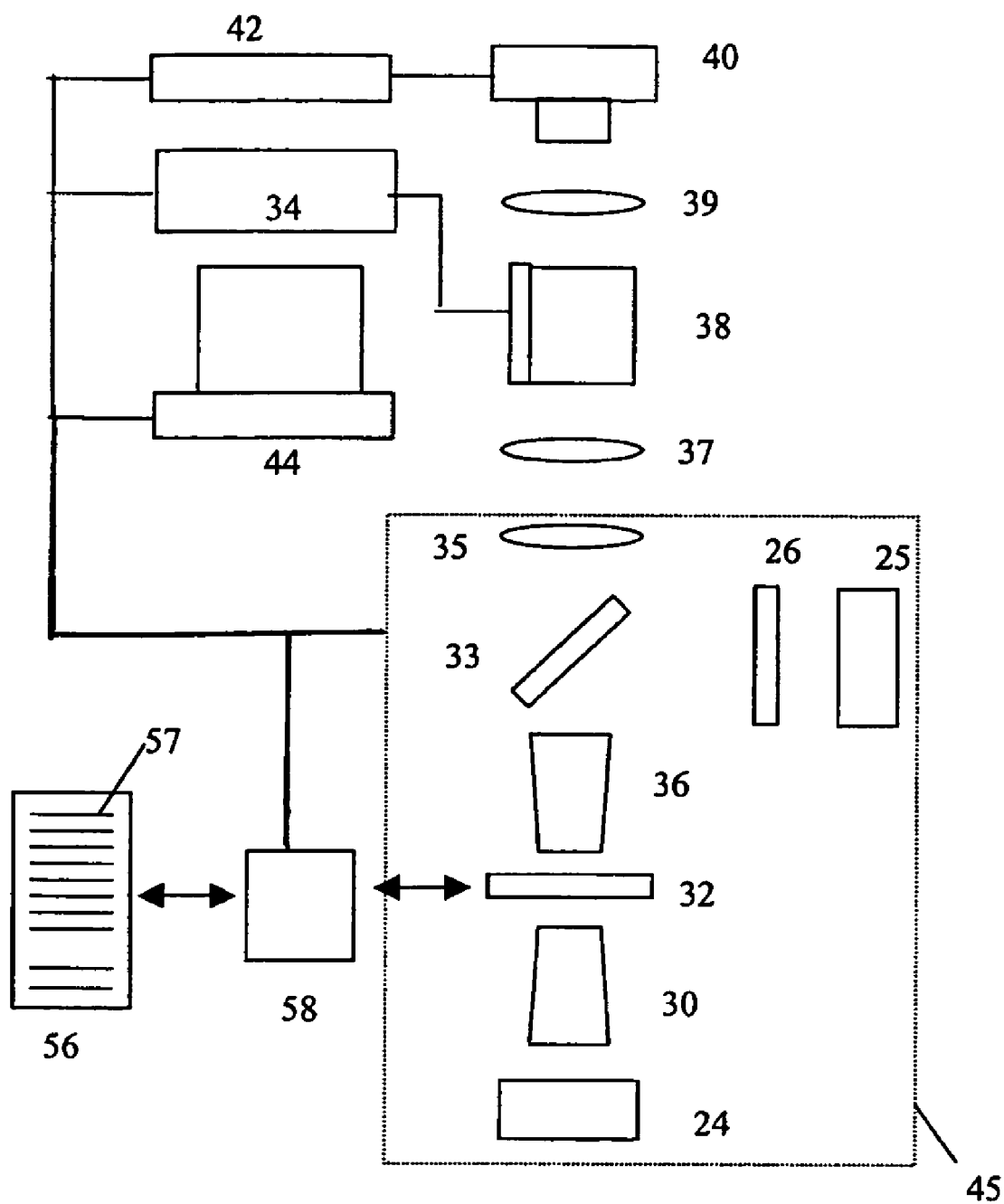
FIG. 3 is a diagram of an apparatus which may be used to carry out the method of the present disclosure.

Turning now to FIG. 3, that figure is a schematic of a light microscope/imaging system constructed according to the teachings of the present disclosure. In FIG. 3, a microscope 45 is shown. An arc lamp or other light source 24 produces light used for transmission illumination through bright-field condenser 30. Light from the bright-field condenser 30 is used to illuminate a sample (not shown) held in a sample plane 32. An objective lens 36 is responsive to the light coming from the sample. The light gathered by the objective lens 36 passes through a beam splitter 33 and through the microscope tube lens 35. For the fluorescence imaging, a second arc lamp or other light source 25 is used to produce light which passes through an excitation filter 26 and is directed by the beamsplitter 33 into the objective 36. The light output from the tube lens 35 enters an AOTF input coupling optic 37 and enters AOTF 38 which is under the control of the AOTF electronics 34.

The light output from the AOTF 38 passes through an AOTF output coupling optic 39 before being input to the CCD camera 40. The CCD camera 40 is under the control of a CCD controller 42.

Completing the description of FIG. 3, a cassette 56 carries a plurality of slides 57, each carrying a sample to be imaged and analyzed. A slide handling system 58 automates the process of moving the slides 57 between the image plane 32 and cassette 56. Objective 36 choice and focus position, sample position in the sample plane 32 as well as other microscopic functions are automated. The workstation 44 controls all functions of the components shown in the figure.

Figure 4:
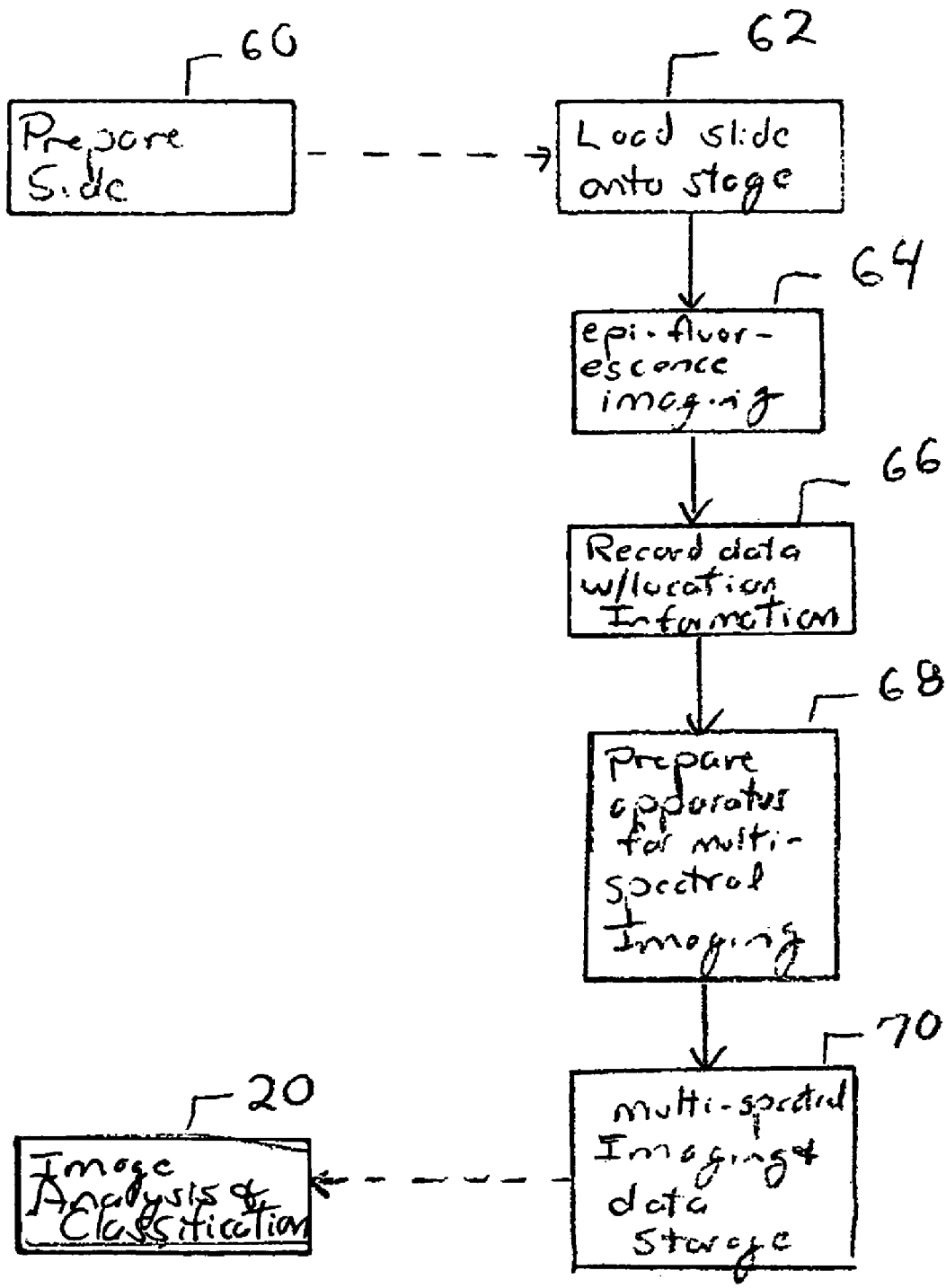
FIG. 4 is a flow chart illustrating one method of operating the apparatus of FIG. 3.

Operation of the apparatus shown in FIG. 3 will now be described in conjunction with FIG. 4 for purposes of illustration and not limitation. Those of ordinary skill in the art will recognize that other apparatus and other methods of operating such apparatus are possible while remaining within the scope of the present disclosure.

In one embodiment of the present disclosure, a cervical sample is taken with a cervical swab and immersed in liquid Pap medium to which are added antibodies of specific high-risk oncogenic markers that are fluorescently tagged. A portion of the Pap stained-fluorescently labeled cells is distributed in a thin monolayer on a microscope slide as represented by slide preparation step 60 of FIG. 4. The prepared slide 57 is placed in the multislide cassette 56 and the cassette 56 attached to the imaging system. Slide preparation is normally performed ahead of time. Slides could be prepared by one lab or organization and shipped to another lab or organization for imaging and analysis. Thus, it is anticipated that all of the steps illustrated in FIG. 4 need not occur one after the other, or even be performed by the same entities.

In step 62, each slide 57 is sequentially and automatically loaded onto the stage of the automated fluorescence-multispectral microscope. The step 62 of FIG. 4 is similar to the step 16 of FIG. 2.

Figures 5A, 5B, 5C:
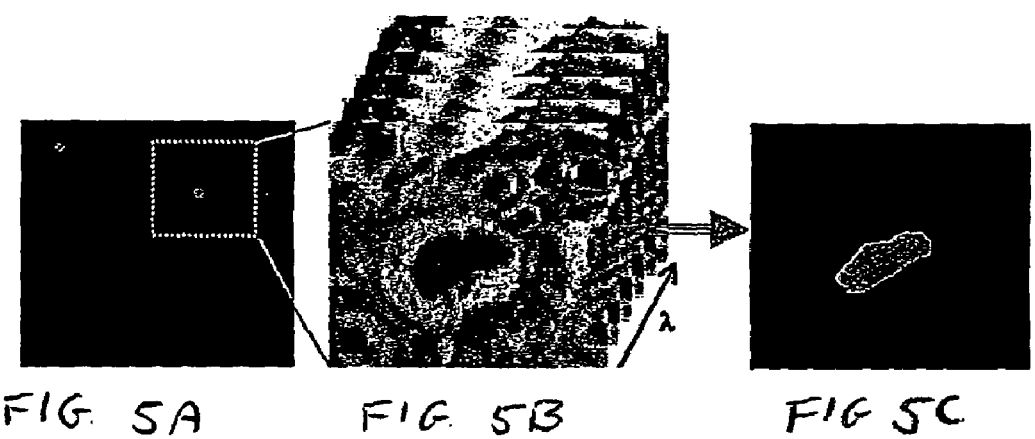
FIGS. 5A, 5B and 5C represent detection of fluorescence at two locations in a sample, a group of transmission images taken using an AOTF at a plurality of different wavelengths for one of the detected locations in FIG. 5A, and the result of the spectra-morphological analysis revealing the presence of HSIL, respectively.

The slide is imaged in epi-fluorescence at, for example, a 10× magnification at step 64. The microscope stage is placed under automated control enabling successive visualization of 50 to 100 fields of view through the slide. The multiple fluorescence and/or phosphorescence labels are chosen to provide "zero background" signal; detection of a signal therefore represents the presence of the HPV markers in question at that location, which data is recorded at step 66. The image produced at this step may appear as shown in FIG. 5A, which shows fluorescence at two locations.

Following completion of this low magnification scan, the apparatus is readied for multi-spectral imaging at step 68. The steps necessary to ready the apparatus for multi-spectral imaging will vary depending on the particulars of each apparatus, but will typically include switching the objective lens 36 to, for example, a 40× magnification, closing the epi-illumination port, removing the fluorescence filters from the light path, and activating the transmission illumination port. The stage is automatically returned to each recorded position where positive fluorescence was detected. At each such position, a series of, for example, approximately thirty images is taken using the high-speed AOTF 38 to step through the wavelengths of interest. The images produced by this step may appear as shown in FIG. 5B. This data may be stored for analysis. The steps 64, 66, 68 and 70 are one example of the data generating step 18 of FIG. 2.

At step 20, which is the same step 20 discussed above in conjunction with FIG. 2, these multispectral image sets are analyzed for spectral and morphological content and classified based on criteria derived from a previously acquired training set. The results for each location are then tabulated for subsequent physician review, and the slide automatically marked at all regions requiring further review. It is contemplated that the step 20 will be performed while the slide is still on the stage, but it need not be. If step 20 is performed while the slide is on the stage, after the sample is analyzed, the slide is removed from the stage, sorted by classification, and the next slide is loaded for repeat of the procedure. A result of such an analysis is shown in FIG. 5C.

The present disclosure provides for an automated Pap screening technology. The present disclosure allows for colabeling of a Pap-stained slide with one or more immunofluorescence dyes targeted to high-risk cancer markers such as HPV. The use of a multiply-labeled single slide allows for improved sensitivity without compromising efficiency. In addition to its application to automated screening, the present disclosure facilitates the pathologist's understanding of the natural history of cervical HPV infections, and thus enables improved predictive skills for determining a women's risk of developing cervical cancer. The present disclosure helps relieve the ever increasing shortage of qualified cytopathologists required to perform conventional manual Pap screening. Additionally, the present disclosure provides for the use of multispectral imaging and analysis to enhance morphometric detection of abnormal cells. Further, the present disclosure provides for the use of an acousto-optic tunable filter (AOTF) based imaging system to provide maximum spectral flexibility and speed in acquisition of this multispectral imaging data. Use of this technology is helpful in the development of an instrument with sufficient throughput to handle the volume of Pap slides which must be examined.

While the present disclosure has been described in conjunction with presently preferred embodiments, those of ordinary skill in the art will recognize that many modifications and variations are possible. The present disclosure is intended to be limited only by the scope of the following claims and not by the scope of the disclosed exemplary embodiments.

What is claimed is:

1. A method of screening for cervical cancer in a cervical cell sample, comprising:
   optically detecting emissions from a label having emission properties outside the visible range from said cervical cell sample for signs of the human papilloma virus; and
   transmission imaging in the visible range from said cervical cell sample for morphological signs of cervical cancer,
   wherein said optically detecting emissions and said transmission imaging include utilizing an AOTF.

2. The method of claim 1 wherein said optically detecting emissions from a label having emission properties outside the visible range includes imaging emissions from labels that emit in the infrared region of the spectrum.

3. The method of claim 2 wherein said transmission imaging in the visible range and imaging emissions from outside the visible range are performed automatically.

4. The method of claim 1 wherein said transmission imaging in the visible range includes transmission imaging at a plurality of wavelengths in the visible range.

5. A method of screening for cervical cancer in a cervical cell sample, comprising:
   optically detecting emissions from at least one wavelength outside the visible range from said cervical cell sample for signs of the human papilloma virus; and
   transmission imaging at a plurality of wavelengths in the visible range from said cervical cell sample for morphological signs of cervical cancer,
wherein said optically detecting emissions and said transmission imaging include utilizing an AOTF.

6. The method of claim 5 wherein said optically detecting emissions from outside the visible range includes imaging emissions from labels that emit in the infrared region of the spectrum.

7. The method of claim 6 wherein said transmission imaging in the visible range and imaging emissions from outside the visible range are performed automatically.

* * * * *